United States Patent
Wang et al.

(10) Patent No.: US 12,419,776 B2
(45) Date of Patent: Sep. 23, 2025

(54) WEARABLE WASTE REMOVAL AND CLEANSING APPARATUS

(71) Applicant: CHIN SHEN HEALTH MANAGEMENT CONSULTANT CO., Taipei (TW)

(72) Inventors: Chia-Koun Wang, Taipei (TW); Shuo-Han Chang, Taipei (TW)

(73) Assignee: CHIN SHEN HEALTH MANAGEMENT CONSULTANT CO., Taipei (TW)

( * ) Notice: Subject to any disclaimer, the term of this patent is extended or adjusted under 35 U.S.C. 154(b) by 0 days.

(21) Appl. No.: 17/749,101

(22) Filed: May 19, 2022

(65) Prior Publication Data

US 2022/0370231 A1 Nov. 24, 2022

(30) Foreign Application Priority Data

May 21, 2021 (TW) ................................. 110118572

(51) Int. Cl.
*A61F 5/442* (2006.01)
*A61F 5/44* (2006.01)
(Continued)

(52) U.S. Cl.
CPC ............ *A61F 5/442* (2013.01); *A61F 5/4408* (2013.01); *A61G 9/02* (2013.01); *A61F 5/451* (2013.01)

(58) Field of Classification Search
CPC ........ A61F 5/442; A61F 5/451; A61F 5/4408; A61G 9/02
See application file for complete search history.

(56) References Cited

U.S. PATENT DOCUMENTS 5,342,583 A * 8/1994 Son .................... A61F 5/451
  4/453
5,681,297 A * 10/1997 Hashimoto ......... A61F 5/451
  119/164
(Continued)

FOREIGN PATENT DOCUMENTS

CN 103750939 A 4/2014
CN 105534632 A 5/2016
(Continued)

OTHER PUBLICATIONS

European Extended Search Report mailed Oct. 25, 2022 in counterpart European application EP 22174339.6, 7 pages in English.
(Continued)

*Primary Examiner* — Guy K Townsend
*Assistant Examiner* — Peter Daniel Smith
(74) *Attorney, Agent, or Firm* — Juan Carlos A. Marquez; Marquez IP Law Office, PLLC (57) ABSTRACT

The present invention discloses a wearable waste removal and cleansing apparatus, comprising a wearable part, a receptacle part detachably connected to the wearable part, and a control assembly connected to the receptacle part for automatic flushing. The wearable part includes a sliding sleeve and wearable pants connected to the sliding sleeve. An engaging mechanism is disposed between the sliding sleeve and the receptacle part. The wearable waste removal and cleansing apparatus of the present invention is simple in structure, convenient to operate, and sanitary and intelligent, and therefore is suitable for popularization and application.

11 Claims, 7 Drawing Sheets

(51) Int. Cl.
    *A61F 5/451*    (2006.01)
    *A61G 9/02*     (2006.01)

(56) References Cited

U.S. PATENT DOCUMENTS

| | | | |
|---|---|---|---|
| 6,394,988 | B1 | 5/2002 | Hashimoto |
| 8,070,736 | B2 * | 12/2011 | Nishtala .................... A61F 5/44 |
| | | | 604/327 |
| 10,100,506 | B2 * | 10/2018 | Sang ........................ A61G 9/003 |
| 10,316,503 | B2 * | 6/2019 | Lu ............................ A61G 9/00 |
| 2002/0010446 | A1 | 1/2002 | Maimets |
| 2004/0176746 | A1 | 9/2004 | Ferral |
| 2011/0282311 | A1 * | 11/2011 | Nishtala ................ A61F 5/4405 |
| | | | 604/332 |
| 2016/0310313 | A1 * | 10/2016 | Saitoh ..................... A61F 5/451 |
| 2016/0331599 | A1 * | 11/2016 | Saitoh ..................... A61F 5/442 |
| 2022/0008273 | A1 * | 1/2022 | Lu ........................... A61G 9/006 |

FOREIGN PATENT DOCUMENTS

| | | | |
|---|---|---|---|
| CN | 106796213 | A | 5/2017 |
| CN | 206151707 | U | 5/2017 |
| CN | 107049586 | A | 8/2017 |
| CN | 105534632 | * | 9/2017 |
| CN | 105534632 | B * | 9/2017 |
| CN | 108113828 | A | 6/2018 |
| CN | 207520258 | U | 6/2018 |
| CN | 108553241 | A | 9/2018 |
| CN | 108720984 | A | 11/2018 |
| JP | H08322868 | A | 12/1996 |
| JP | 2000232986 | A | 8/2000 |
| JP | 2001190583 | A | 7/2001 |
| JP | 2001314433 | A | 11/2001 |
| JP | 2012525906 | A | 10/2012 |
| JP | 2016022125 | A | 2/2016 |
| JP | 2015154901 | A | 8/2016 |
| KR | 101595434 | B1 | 2/2016 |
| KR | 20160110936 | A | 9/2016 |
| TW | I712405 | B | 12/2020 |

OTHER PUBLICATIONS

Taiwan Office Action and Search Report mailed Dec. 26, 2022 in counterpart Taiwan application TW110118572, 10 pages in Chinese.
Taiwan Search Report mailed Dec. 26, 2022 in counterpart Taiwan application TW110118572, 1 page in Emglish.
Japanese Office Action mailed Jul. 10, 2023 in counterpart Japanese application JP 2022083076, 7 pages in Japanese.
Japanese Office Action mailed Jul. 10, 2023 in counterpart Japanese application JP 2022083076, 8 pages in English.
Canadian Office Action mailed Jul. 10, 2023, in counterpart Canadian application 2022-083076, 5 pages in English.
Korean Office Action mailed Nov. 24, 2023 in counterpart Korean application KR 10-2022-0061686, 6 pages in Korean.
Japanese Office Action mailed Apr. 15, 2024 in counterpart Japanese application JP2022-083076, 6 pages in Japanese.
Japanese Office Action mailed Apr. 15, 2024 in counterpart Japanese application JP2022-083076, 6 pages in English.
Canadian Office Action mailed Sep. 20, 2024 in counterpart Canadian application CA3,159,455, 5 pages in English.
European Examination Report mailed Mar. 31, 2025 in counterpart European application EP 22 174 339.6, 6 pages in English.
Chinese Office Acion mailed May 14, 2025 in counterpart Chinese application CN 202110561980.2, 10 pages in Chinese.

* cited by examiner

WEARABLE WASTE REMOVAL AND CLEANSING APPARATUS

BACKGROUND OF THE INVENTION

1. Field of the Invention

The present invention relates to the field of patient care, and in particular, to a wearable waste removal and cleansing apparatus.

2. Description of the Related Art

For bedridden patients, it is essential for caregivers to assist the patient in all areas of personal hygiene, including bodily waste disposal. Common methods include providing waterproof bed covers and use of a urinal or bedpan for collection and disposal. Therefore, nursing intensity is high, and probability that the patient suffers from bedsores or even ulceration is increased. At present, disposable adult diapers may also be used. Despite improvements in permeability and comfort, such diapers require manual replacement every time. Therefore, costs and working intensity of the caregiver for patients who are bedridden for a long time and unable to care for themselves is still very high, and sanitation still cannot be guaranteed.

Therefore, there is an urgent need to provide a wearable waste removal and cleansing apparatus that is simple in structure, convenient to operate, and sanitary and intelligent, to overcome the noted defects.

SUMMARY OF THE INVENTION

An objective of the present invention is to provide a wearable waste removal and cleansing apparatus that is simple in structure, convenient to operate, and sanitary and intelligent.

In order to achieve the objective, the present invention provides a wearable waste removal and cleansing apparatus, comprising a wearable part, a receptacle part detachably connected to the wearable part, and a control assembly connected to the receptacle part for automatic flushing, the wearable part comprising a sliding sleeve and wearable pants connected to the sliding sleeve, and an engaging mechanism disposed between the sliding sleeve and the receptacle part.

In the wearable waste removal and cleansing apparatus of the present invention, the engaging mechanism is disposed between the wearable part and the receptacle part to implement detachability. During operation, the wearable part is worn by the patient, the receptacle part is connected to the wearable part, and the receptacle contents are automatically flushed using the control assembly. In this way, no manual operation is required, cleanliness and hygiene are improved, and patient comfort is enhanced by means of intelligent automatic operation. After flushing, it is only necessary to remove the receptacle part without having to repeatedly put on and remove the wearable part, a considerably more convenient operation. The present invention is thus more likely to be popular in the field of patient care.

Preferably, the receptacle part includes an upper housing having a receptacle body, and a bottom housing and a rear housing each connected to the upper housing, the engaging mechanism being disposed between the upper housing and the sliding sleeve.

Preferably, a bottom side of the sliding sleeve has at least one slot, a front end of at least the upper housing being detachably engaged with the at least one slot.

Preferably, a first connecting portion is disposed on the sliding sleeve, and a second connecting portion is disposed on the upper housing, corresponding to the first connecting portion.

Preferably, the control assembly includes a connecting element and a detection element configured to be connected to a processing host and the receptacle part.

Preferably, the detection element includes a camera assembly mounted in the upper housing and protruding from the receptacle body to identify excretions in the receptacle body, and a gravity sensor arranged in a receiving space formed between the upper housing and the bottom housing.

Preferably, the connecting element includes an air conduit to supply airflow with positive air pressure to the receptacle body or to extract excretions from the receptacle body with airflow having negative air pressure, and a water conduit to flush the patient's body or the receptacle body.

Preferably, a receiving space is formed between the upper housing and the rear housing and between the upper housing and the bottom housing, the water channel being placed in the receiving space and including a first flushing water conduit, a second flushing water conduit, and a third flushing water conduit which all extend toward the receptacle body.

Preferably, at least a surface layer of the wearable pants is waterproof, and the wearable pants have an excretion opening, a buttock portion around the excretion opening, a crotch portion and a urinary portion connected to the buttock portion, and at least one connecting part detachably wearable to a waist of human body.

Preferably, the buttock portion and the crotch portion each have a multilayered structure, the multilayered structure including a bottom layer, a decompression lining formed on the bottom layer, a sponge layer formed on the decompression lining and having a middle portion bulging upwardly, and a waterproof surface layer formed on the sponge layer.

Preferably, the urinary portion bulges outwardly to form a concave area.

Preferably, an engaging portion configured to accommodate the sliding sleeve is formed on a back circumferential edge of the excretion opening.

PREFERRED EMBODIMENT OF THE PRESENT INVENTION

In order to describe the technical content, structural features, achieved effects of the present invention in detail, detailed descriptions are given in combination with implementations and accompanying drawings as follow.

Figure 1:
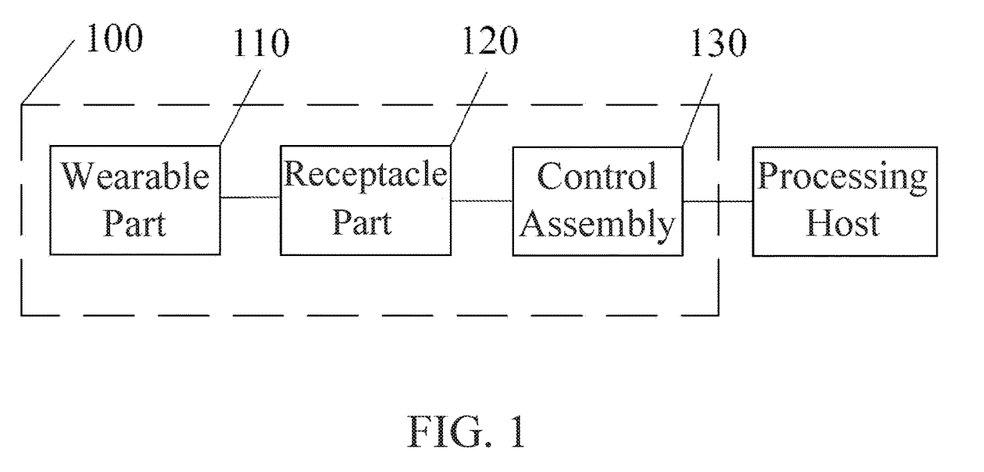
FIG. 1 is a structural block diagram of an embodiment of a wearable waste removal and cleansing apparatus according to the present invention.

A wearable waste removal and cleansing apparatus of the present invention is particularly adapted to be worn by an adult patient. FIG. 1 is a structural block diagram of an embodiment of a wearable waste removal and cleansing apparatus 100 according to the present invention. The wearable waste removal and cleansing apparatus comprises a wearable part 110, a receptacle part 120 detachably connected to the wearable part 110, and a control assembly 130 connected to the receptacle part 120 and a processing host. During the operation, the wearable part 110 is first worn by the patient, then the receptacle part 120 is combined to the wearable part 110, and the patient and the receptacle part 120 are automatically flushed by using the control assembly 130. In this way, the manual operation is not required. After finishing the flushing, it is only necessary to remove the receptacle part 120 without having to put on and off the wearable part 110 repeatedly, which is more convenient to operate.

Figure 2:
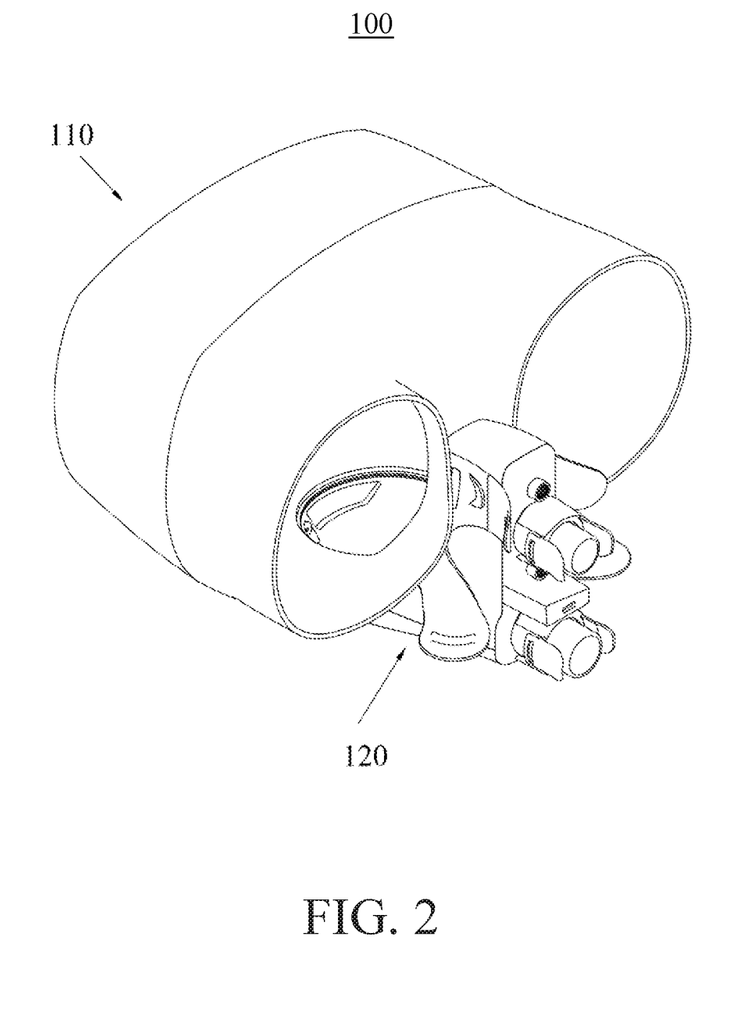
FIG. 2 is a three-dimensional view of an embodiment of a wearable waste removal and cleansing apparatus according to the present invention.
Figure 3:
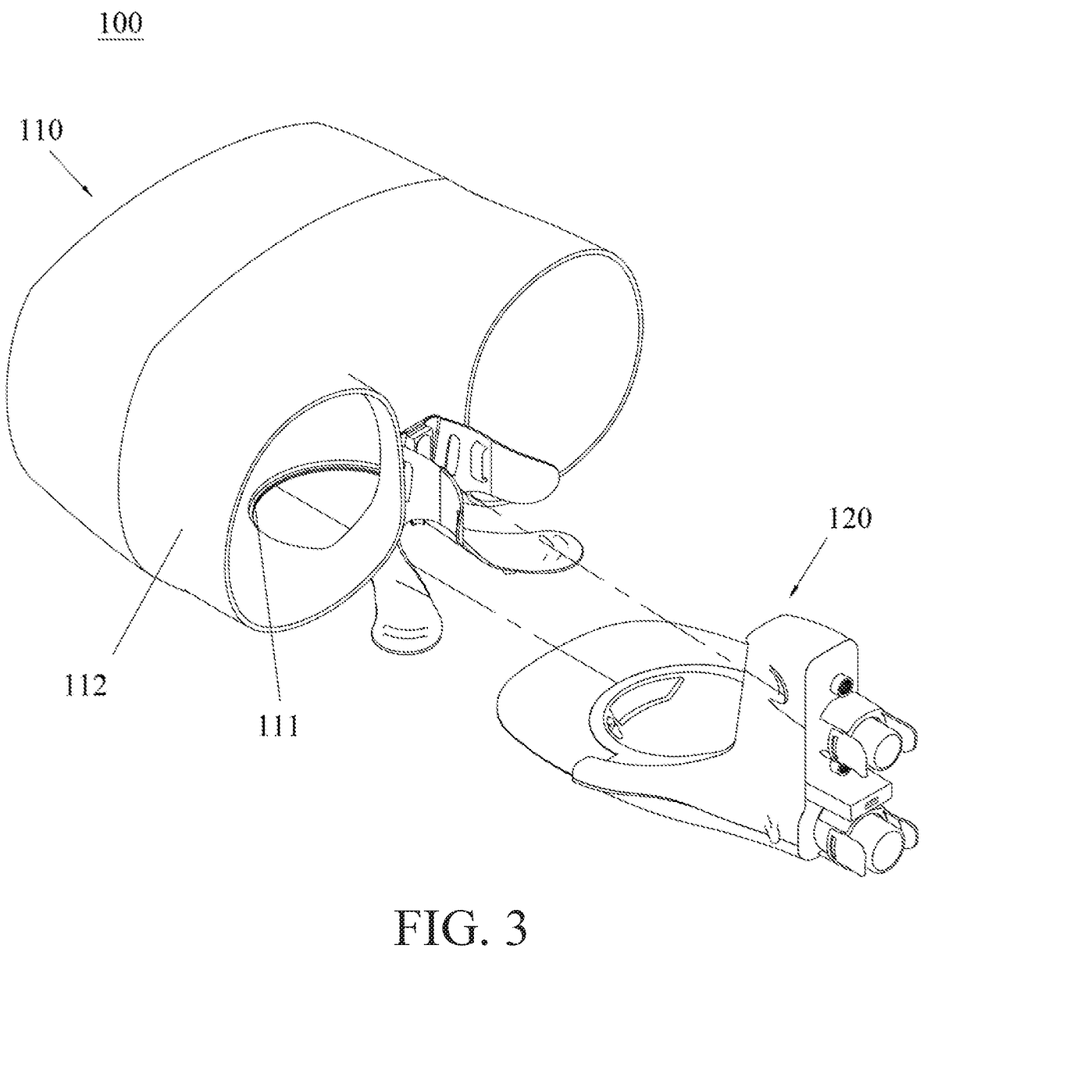
FIG. 3 is a partial exploded view of an embodiment of a wearable waste removal and cleansing apparatus according to the present invention.
Figure 4:
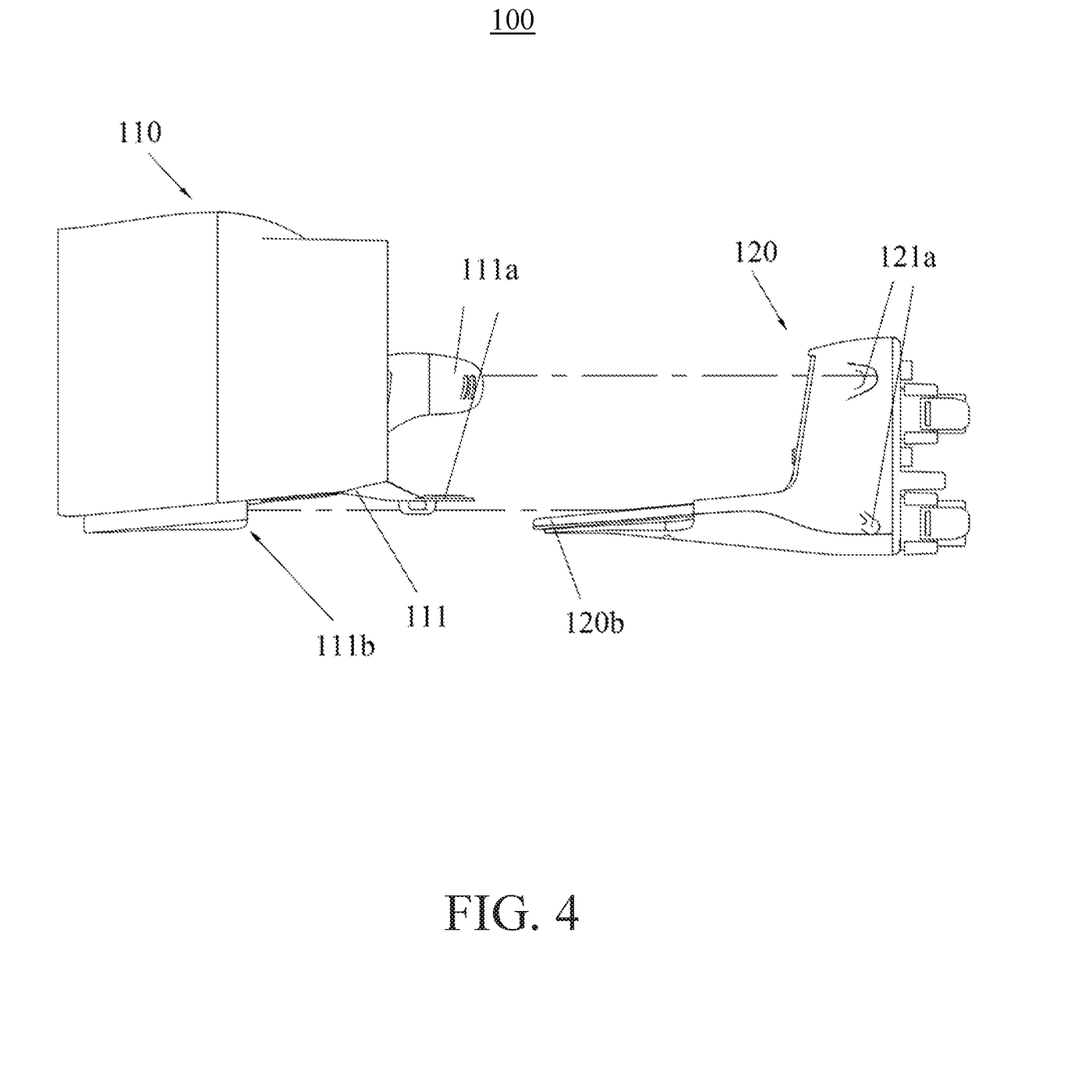
FIG. 4 is an exploded view of an embodiment of a wearable waste removal and cleansing apparatus from another angle according to the present invention.

In more details, as shown in FIG. 2 to FIG. 4, the wearable part 110 includes a sliding sleeve 111 connected to the receptacle part 120, and wearable pants 112 connected to the sliding sleeve 111 and directly worn on a human body. In order to facilitate detachment, an engaging mechanism is arranged between the sliding sleeve 111 and the receptacle part 120. For example, a slot 111b (see FIG. 4) is provided on a bottom side of the sliding sleeve 111, and the receptacle part 120 (for example, a front end 120b of the receptacle part 120, such as a front end of the upper housing or the bottom housing) is snapped into the slot 111b. In addition, a shape and a size of the sliding sleeve 111 match the receptacle part 120.

Figure 6:
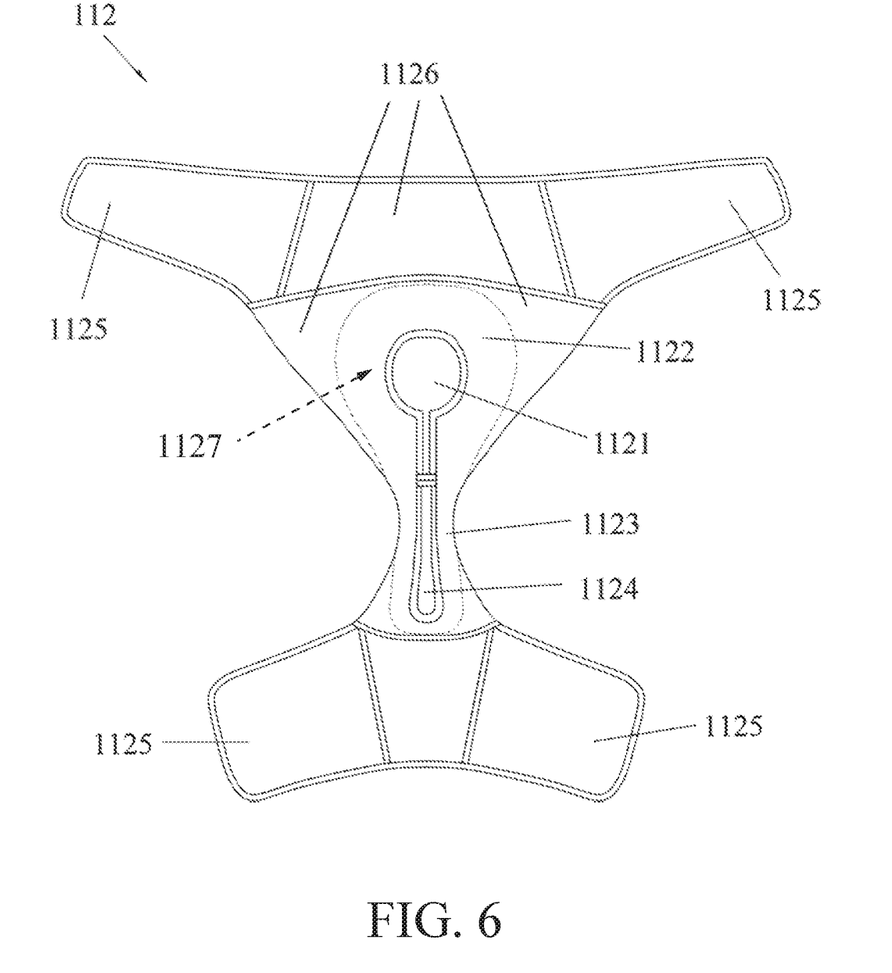
FIG. 6 is a plane view of wearable pants of a wearable waste removal and cleansing apparatus according to the present invention.

As the wearable pants 112 are in direct contact with the human body, the materials of which the wearable pants are made need to be soft, comfortable, waterproof, breathable, antibacterial, or the like. The materials comprise cloth, sponge and plastic material, or the like, and thus the wearable pants have different structures for different portions of the human body. FIG. 6 is a front view of a side of wearable pants expanded and in direct contact with the human body. The wearable pants 112 have an excretion opening 1121 aligned with the receptacle part 120, a buttock portion 1122 around the excretion opening 1121, a crotch portion 1123 and a urinary portion 1124 connected to the buttock portion 1122, and a plurality of connecting parts 1125 detachably wearable to a waist of human body. A plurality of elastic pieces 1126 are formed between the connecting parts 1125 and a middle structure (that is, 1121 to 1124) of the wearable pants 112. The entire surface fabric of the wearable pants is preferably waterproof, skin-friendly, antibacterial, anti-allergic, anti-ozone, and breathable. An elastic tightening belt is disposed along the entire outer edge to facilitate adjustment for patients having different body shapes. A size of the excretion opening 1121 matches that of the receptacle. An edge of the opening is also made of a waterproof material, and an engaging portion 1127 configured to be engaged with the sliding sleeve 111 is formed on a periphery of a back circumferential edge of the opening. Optionally, the engaging portion 1127 is made of plastic material. In this embodiment, the wearable pants 112 and the sliding sleeve 111 are fixedly connected by using the engaging portion 1127, for example, by means of hot pressing.

Figure 7:
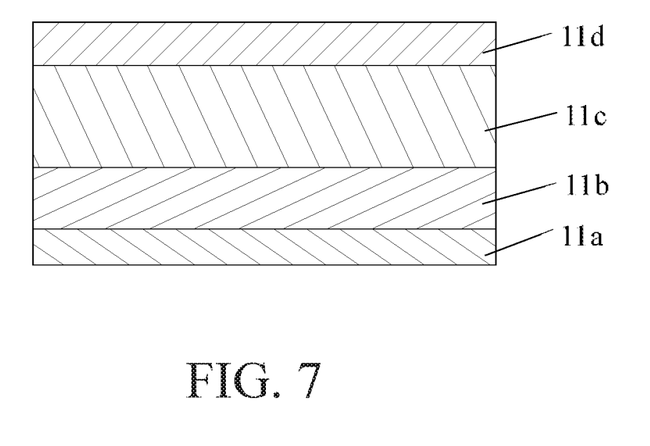
FIG. 7 is a partial cross-section of wearable pants of a wearable waste removal and cleansing apparatus according to the present invention.

As shown in FIG. 7, the buttock portion 1122 and the crotch portion 1123 each are a multilayered structure. The multilayered structure includes a bottom layer 11a, a decompression lining 11b formed on the bottom layer 11a, a sponge layer 11c formed on the decompression lining 11b and having a middle portion bulging upwardly, and a waterproof surface layer 11d formed on the sponge layer 11c. A width of the crotch portion 1123 may be adjusted such that there is no tightness in the inner thigh when the wearable pants are worn. The urinary portion 1124 bulges outwardly (or toward the back side) to form a concave area, and no step difference exists at a junction of the urinary portion 1124 and the crotch portion 1123 to prevent entry of external contaminants.

Each of the connecting parts 1125 is elastic and provided with a hook-and-loop tape structure. An overall size of the connecting parts 1125 at an abdomen portion of human body (that is, the lower connecting parts 1125 shown in FIG. 6) is less than an overall size of the connecting parts 1125 at a waist portion of human body (that is, the upper connecting parts 1125 shown in FIG. 6). The wearable pants 112 are fixed to the body by adjusting the hook-and-loop tape, to prevent dislodging or displacement.

Figure 5:
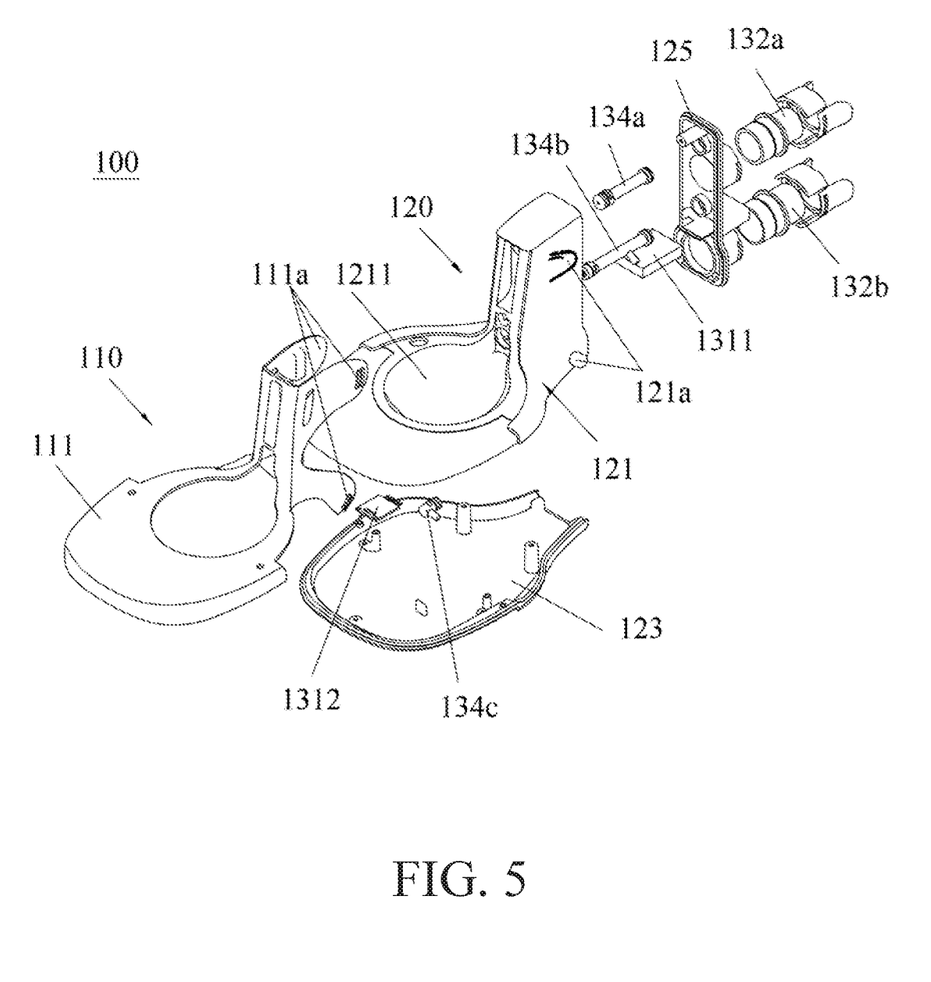
FIG. 5 shows an exploded view of an embodiment of a wearable waste removal and cleansing apparatus according to the present invention, in which wearable pants are not shown.

Referring to FIG. 5, the receptacle part 120 of the present invention includes an upper housing 121 having a receptacle body 1211, and a bottom housing 123 and a rear housing 125 each connected to the upper housing 121. The upper housing 121 and the bottom housing 123 are assembled in a vertical direction, and fastened to each other by screws. A specific receiving space is formed between the upper housing 121 and the bottom housing 123 for arranging a gravity sensor 1312 and other parts therein. The rear housing 125 is mounted to the rear side of the upper housing 121 so that devices and conduits are arranged therein and thus connected to an external processing host. Specifically, an engaging mechanism is provided and disposed between the receptacle body 1211 of the upper housing 121 and the sliding sleeve 111 to facilitate their easy detachment. For example, a front end 120b of the receptacle body 1211 is snapped into an annular slot 111b formed on a bottom side of the sliding sleeve 111. In an exemplary embodiment, a front end of the combination of the upper housing 121 and the bottom housing 123 of the receptacle part 120 is inserted and snapped into the annular slot 111b (see FIG. 4). In addition, a first connecting portion 111a is disposed on the sliding sleeve 111, and a second connecting portion 121a is disposed on the upper housing 121, corresponding to the first connecting portion 111a. The connection between them can be achieved by such as using a hook-and-loop tape or a buckle. For example, the first connecting portion 111a can be in the form of an opening, and the second connecting portion 121a a buckle piece. In another example, the first connecting portion 111a and the second connecting portion 121a are both a hook-and-loop tape. By means of the combination of the engaging mechanism and the first connecting portion 111a and the second connecting portion 121a, the connection between the sliding sleeve 111 and the receptacle body 1211 is more stable, and detachment can be easily and conveniently achieved.

The control assembly 130 of the present invention includes a connecting element configured to be connected to the receptacle part 120 and the processing host, and a detection element configured to implement some specific functions, and may further include control members (not shown) configured to control the entire elements (e.g., the connecting element and the detection element). Preferably, the connecting element includes an air conduit and a water conduit. The air conduit is connected to the external processing host to supply airflow with positive air pressure to the receptacle body 1211 or to evacuate excretions from the receptacle body 1211 with an airflow having negative air pressure. The water conduit is connected to the air conduit to flush the patient's body and clean the receptacle body 1211. It can be understood that the air conduit comprises an air supply passage 132*a* and a suction passage 132*b* (only some joints or conduits are shown in the air conduit in the figure), and the dirt is evacuated to the external processing host through the suction passage 132*b*. In the present invention, the water conduit comprises a first flushing water conduit 134*a* for flushing the urethra, a second flushing water conduit 134*b* for flushing the anus, and a third flushing water conduit 134*c* for cleaning the receptacle body 1211 (only some joints or conduits of the water conduit are shown in the figure). The first flushing water conduit 134*a* and the second flushing water conduit 134*b* are disposed in a receiving space between the upper housing 121 and the rear housing 125, and their outlet positions are disposed vertically to adapt to the human organs. The third flushing water conduit 134*c* may be disposed in a receiving space between the upper housing 121 and the bottom housing 123 to optimize the space layout. In detail, the external processing host can provide clean water to the first flushing water conduit 134*a*, the second flushing conduit 134*b* and the third flushing water conduit 134*c*. The excretions in the receptacle body 1211 can be directly evacuated to the external processing host through the suction passage 132*b*. Alternatively, clean water can be introduced from the third flushing water conduit 134*c* to the receptacle body 1211, thereby softening excretions such as stool after which the mixture of excretions and water is evacuated to the external processing host through the suction passage 132*b*. Following evacuation of the excretions, the patient's body is flushed and cleaned by water introduced from a corresponding one of the first flushing water conduit 134*a* and the second flushing water conduit 134*b*, or from both, each flushing a corresponding area of the patient's body. After flushing, wastewater is evacuated to the external processing host through the suction passage 132*b* and the third water conduit 134*c* further introduces clean water to flush and clean the receptacle body 1211. After flushing, fouled water is evacuated from the receptacle body 1211 to the external processing host through the suction passage 132*b* and the air supply conduit 132*a* supplies airflow to dry the body and the receptacle body 1211.

It should be noted that, in an exemplary embodiment, positive air pressure in the air supply passage 132*a* supplies airflow to the receptacle body 1211 while negative air pressure in the suction passage 132*b* evacuates contents of the receptacle body 1211 or wastewater generated by flushing operations. Accordingly, the space within the receptacle body 1211 can be considered to connect of water conduit and air conduits to arrive at the flushing and evacuation operations.

Preferably, the present invention further improves intelligence of the product with the detection element. As shown in FIG. 5, the detection element includes a camera assembly 1311 mounted in the upper housing 121 and protruding from the receptacle body 1211 to focus on the excretions on the receptacle body 1211 for identification, and different modes of the water conduit and the air conduit are controlled according to the different types of excretions identified. In addition, the detection element further includes a gravity sensor 1312 arranged in the receiving space formed between the upper housing 121 and the bottom housing 123 to detect whether a wearer turns over or turns. It should be noted that the above mounting position of the control assembly is merely a preferred embodiment, and is not intended to limit the present invention.

Accordingly, in the wearable waste removal and cleansing apparatus 100 of the present invention, the engaging mechanism is disposed between the wearable part 110 and the receptacle part 120 to implement detachability. During the operation, the wearable part 110 is donned by the patient, then the receptacle part 120 is connected to the wearable part 110. The patient and the receptacle part 120 are thus automatically flushed by the control assembly 130. In this way, no manual operation is required, thereby improving cleanness and hygiene, and further improving the patient comfort by means of intelligent automatic operation. After flushing, it is only necessary to remove the receptacle part 120 without any requirement to repeatedly put on and take off the wearable part 110, a considerably more convenient operation. The present invention is adapted to be popularized in the field of patient care.

The disclosure merely provides preferable embodiments of the present invention, none of which is intended to limit the patent scope thereof. Therefore, any equivalent changes made according to the recitation will be understood to still fall well within the scope of the present invention.

What is claimed is:

1. A wearable waste removal and cleansing apparatus, comprising:
   a wearable part worn by a patient, the wearable part comprising waterproof wearable pants worn on a human body of the patient, and a sliding sleeve connected to the wearable pants and formed so as to be located at a buttock portion of the wearable pants relative to the human body;
   a receptacle part formed so as to be detachably connectable to the sliding sleeve and positioned only at the buttock portion of the human body while connected to the sliding sleeve; and
   a control assembly connected to the receptacle part for automatic flushing, the control assembly including a connecting element operatively configured to evacuate excretions from the receptacle part and to flush the receptacle part so as to avoid removal of the waterproof wearable pants after excretion evacuation and flushing;
   wherein the wearable part further comprising an engaging mechanism being disposed between the sliding sleeve and the receptacle part, and being configured such that the receptacle part is able to directly and detachably connect to at least one slot provided on a bottom side of the sliding sleeve when the wearable pants is worn on a human body of the patient, and
   wherein the receptacle part comprises an upper housing having a receptacle body and the engaging mechanism is disposed between the upper housing and the sliding sleeve, the engaging mechanism comprising:
   a front end of the upper housing of the receptacle part and the at least one slot formed on the bottom side of the sliding sleeve, the front end of the upper housing of the receptacle part being detachably inserted and snapped into the at least one slot, and
   a first connecting portion disposed on the sliding sleeve outside the at least one slot, and a second connecting portion being disposed on the upper housing and corresponding to the first connecting portion, the first connecting portion being detachably connectable to the second connecting portion.

2. The wearable waste removal and cleansing apparatus according to claim 1, wherein the receptacle part further comprises a bottom housing and a rear housing each connected to the upper housing.

3. The wearable waste removal and cleansing apparatus according to claim 2, wherein the at least one slot formed on the bottom side of the sliding sleeve is an annular slot.

4. The wearable waste removal and cleansing apparatus according to claim 2, wherein the control assembly comprises a detection element configured to be connected to a processing host and the receptacle part.

5. The wearable waste removal and cleansing apparatus according to claim 4, wherein the detection element comprises a camera assembly mounted in the upper housing and protruding from the receptacle body to identify excretions on the receptacle body, and a gravity sensor arranged in a receiving space formed between the upper housing and the bottom housing.

6. The wearable waste removal and cleansing apparatus according to claim 4, wherein the connecting element comprises:
   an air conduit comprising an air supply passage to supply an airflow with positive air pressure to the receptacle body and a suction passage to evacuate excretions from the receptacle body with an air flow having negative air pressure; and
   a water conduit to flush the patient's body or the receptacle body.

7. The wearable waste removal and cleansing apparatus according to claim 6, wherein a receiving space is formed between the upper housing and the rear housing and between the upper housing and the bottom housing, the water conduit being placed in the receiving space and comprising a first flushing water conduit, a second flushing water conduit, and a third flushing water conduit which all extend toward the receptacle body.

8. The wearable waste removal and cleansing apparatus according to claim 1, wherein at least a surface layer of the wearable pants is waterproof, and the wearable pants have an excretion opening formed at the buttock portion, a crotch portion and a urinary portion connected to the buttock portion, and at least one connecting part detachably wearable to a waist portion of human body.

9. The wearable waste removal and cleansing apparatus according to claim 8, wherein the buttock portion and the crotch portion each are a multilayered structure, the multilayered structure comprising a bottom layer, a decompression lining formed on the bottom layer, a sponge layer formed on the decompression lining, and a waterproof surface layer formed on the sponge layer.

10. The wearable waste removal and cleansing apparatus according to claim 8, wherein the urinary portion bulges outwardly to form a concave area.

11. The wearable waste removal and cleansing apparatus according to claim 8, wherein an engaging portion configured to be engaged with the sliding sleeve is formed on a back circumferential edge of the excretion opening.

* * * * *